US005702404A
US005702404A

United States Patent [19]
Willingham

[11] Patent Number: 5,702,404
[45] Date of Patent: Dec. 30, 1997

[54] STOOL EXTRACTOR

[76] Inventor: Suzan E. Willingham, 1204 J.J. Flewellen, Waco, Tex. 76704

[21] Appl. No.: 656,764

[22] Filed: Jun. 3, 1996

[51] Int. Cl.$^6$ ............................................. A61B 17/42
[52] U.S. Cl. ................................. 606/122; 604/317
[58] Field of Search ............................. 606/122, 124, 606/127, 207; 604/317, 54

[56] References Cited

U.S. PATENT DOCUMENTS 3,088,465  5/1963  Smith ............................. 606/122

*Primary Examiner*—Michael Buiz
*Assistant Examiner*—Kevin Truong
*Attorney, Agent, or Firm*—John E. Vandigriff

[57] ABSTRACT

The invention is to a two part instrument used in removing fecal impaction. The two parts each include a handle and a spoon shaped member attached to each handle. One handle has a tongue and the other a groove which are placed to gather to hold the handles secured together during removal. The handles have ridges or a textured surface to provide a non-slip grip.

7 Claims, 3 Drawing Sheets

STOOL EXTRACTOR

FIELD OF THE INVENTION

This invention relates to surgical instruments for rectal treatment, and more particularly to an instrument for removing fecal impaction or otherwise detained stool from the rectum of a patient.

BACKGROUND OF THE INVENTION

The inability to expel fecal matter from the rectum can become a serious problem for stroke and spinal cord injury victims, the elderly, and the debilitated. When suppositories, laxatives, and enemas do not effectively remove the stool, the usual treatment is for a nurse to remove it little by little with a gloved finger. This presents several problems such as severe discomfort or pain, rectal tears, and bleeding. Further complications arise if the stool is too hard and large, or too soft and clay-like to grasp with a finger and pull out. The procedure can be quite time-consuming and messy for the nurse, and quite humiliating, painful, traumatic, and debilitating to the patient. For this reason, patients and nurses alike dread the prospect of having to resort to this type of treatment. Therefore, there is a tendency sometimes to delay assessment of the situation in hopes that the problem will somehow resolve itself or will be discovered and dealt with at a more convenient time. This tendency to delay assessment further compounds the difficulty in removing the stool since it allows for further build-up with increased difficulties and discomfort to the patient.

Various instruments have been devised for the removal of fecal impaction from a person's rectum. One prior art instrument is in the form of a scissor that has two parts hinged together, and a pair of handles for separating cupped ends.

U.S. Pat. No. 2,644,455, discloses a scissor-like instrument for removal of fecal impaction. This type instrument must be inserted in the rectum partially opened in order to catch hold of the stool mass. This partially opened instrument will tend to add discomfort to the patient since the rectal opening has to be spread to insert the instrument. It also would be difficult to maneuver around the whole of the stool mass.

Another prior art instrument is disclosed in U.S. Pat. No. 3,022,787.

U.S. Pat. No. 5,000,750, describes a tube and augur arrangement. The tube must be inserted, and then the augur turned. The limited space between the legs of the patient is inconvenient for turning the augur handle, and there appears to be a risk of injury to the bowel wall when such an instrument is used.

SUMMARY OF THE INVENTION

The present invention alleviates the pain and trauma associated with removing impacted feces or detained stool due to weakened abdominal and perineal muscles. It allows for quick removal and easier clean-up since no water is necessary. It alleviates embarrassment and humiliation to the patient since he/she knows an instrument is being used instead of someone else's finger, and is not required so much of the nurses's time. These factors remove the dread associated with feces' removal. Therefore patients and nurses can assess for the problem without the hesitancy often associated with the dread of removing impacted or detained stool. Patient care will then improve and the possibility of further medical complications will decrease.

The advantage of this invention over others designed for this use is that: (1) it provides two separate pieces designed to be maneuvered completely around the fecal matter to pull it out in total if not too large, rather than a small piece at a time, thus saving time; (2) For a large, hard fecal impaction, the insertion of one spoon head provides a firm surface to press the stool against to break it up using a gloved finger rather than trying to press it against the soft, fragile bowel wall, thus preventing pain, rectal or anal trauma, and the possibility of bowel rupture; (3) it needs no water, thus eliminating much of the mess associated with other interventions, and/or the use of enemas that the nurse thought would be unsuccessful but were given anyway in a vain attempt to try to avoid the dreaded traditional digital extraction; (4) it has safety features which provide for comfort and ease in insertion, and which prevent the danger of pinching or injuring the bowel wall; (5) it can be made of plastic and is therefore cost effective; and (6) it can be washable and reusable for the same patient which adds to its cost effectiveness and decreases environmental waste.

The invention is to a two-piece instrument that may be made of stainless steel for sterilization and reuse, or of inexpensive plastic that may be packaged for one time or multiple use for one patient with proper cleansing and storing between uses. The two pieces each have a spoon shaped end and an angled neck between the spoon shaped end and the handle. The angled necks allow the handles and spoon shaped ends to be crossed for holding the fecal impaction between the two spoon shaped ends. One handle has a groove extending the length of the handle, and the other handle has a tongue that extends out of the handle and resides in the groove of the other handle to prevent slipping or separation of the two parts during removal of the stool.

In use, one spoon is inserted at a time around the fecal matter. After the second spoon is inserted the two are joined at the handles to secure the two pieces together. There is less chance of damaging the rectal wall because of the rounded tips of the spoons, and the two spoons do not touch when the handles are joined together, eliminating the chance of pinching the rectal wall.

The technical advance represented by the invention, as well as the objects thereof, will become apparent from the following description of a preferred embodiment of the invention when considered in conjunction with the accompanying drawings, and the novel features set forth in the appended claims.

DESCRIPTION OF A PREFERRED EMBODIMENT

Figure 1:
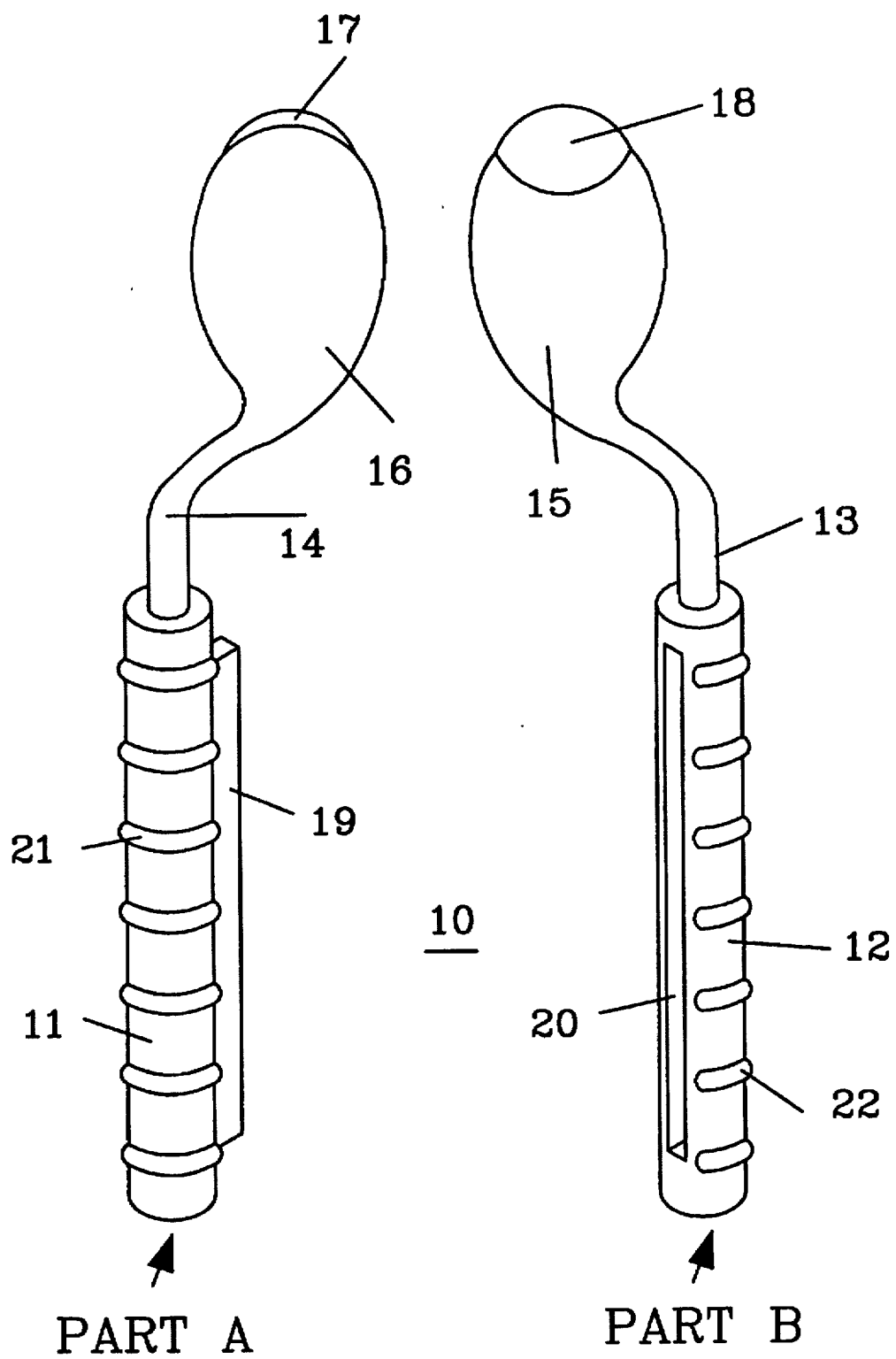
FIG. 1 illustrates the two pieces of the two-piece instrument.

The invention is to a two-piece instrument 10 used in fecal removal. FIG. 1 shows the two separate pieces, identified as Part A and Part B, where Part B has a handle 12 having a grove 20 therein. On handle 12 are ridges to prevent the handle from slipping from the hand during used. Attached to one end of handle 12 is a neck 13 which extends axial to handle 12 and then is curved to one side. At the end of the curved part 13 is spoon shaped part 15. The end of spoon shaped part 15, opposite the end attached to curved part 13 is a rounded thicker section 18.

This section is the first part inserted into the rectum during stool removal, and is rounded and thickened to provide a rounded smooth edge. A narrow thin edge could possibly damage or cut the rectum wall, but the rounded thicker edge does not hurt or injure the rectal wall.

The second piece of two-part instrument 10 is Part A which is similar, in most respects to Part B. On part A, handle 11 has ridges 21 to provide a better grip on the handle, but where handle 12 has a groove 20, handle 11 has a tongue 19 that extends from the surface of handle 12. Tongue 19 is shaped to fit into groove 20 in handle 12.

Extending axially from handle 11 is neck 14 which, similar to neck 13, bends and terminates in spoon part 16. Spoon part 16 terminates in rounded, thickened part 17.

Figure 2:
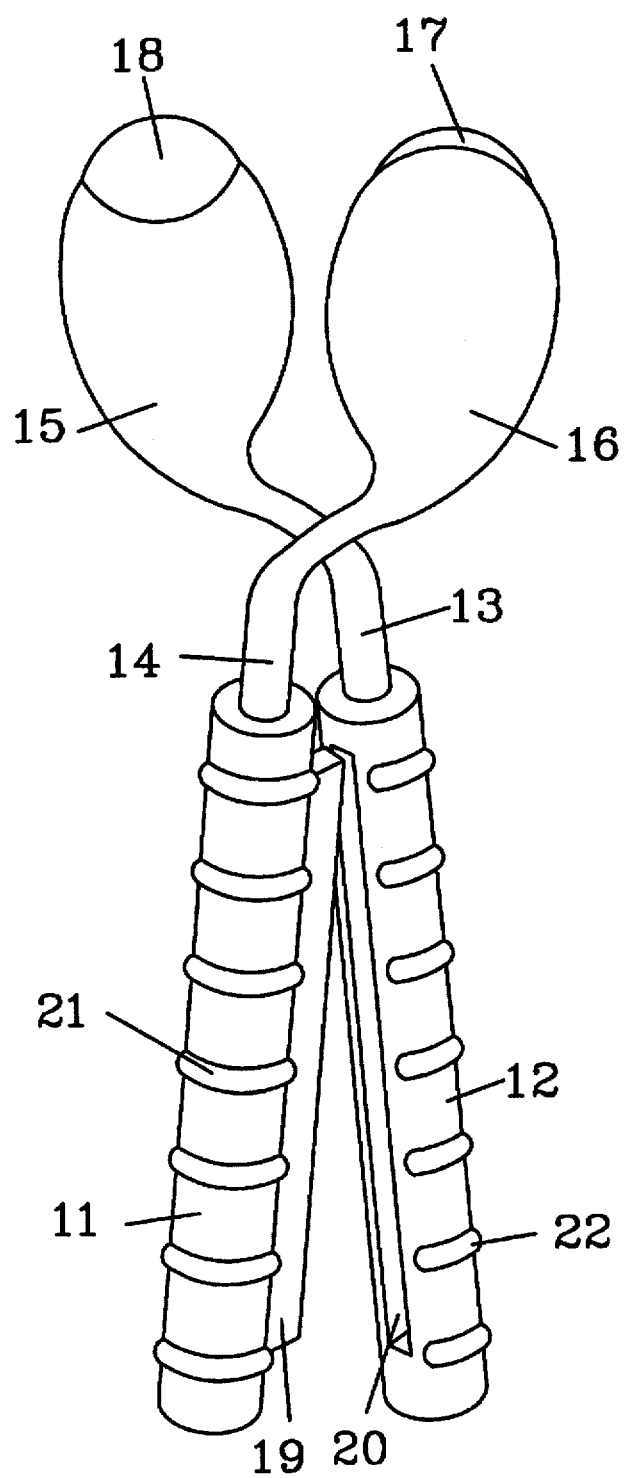
FIG. 2 illustrates the two piece instrument with neck portions crossed.

FIG. 2 shows the two parts of instrument 10 partially together. Assuming that Part B is in place, having inserted in the rectum, then Part A is inserted at an angle and then joined to Part B.

Figure 3:
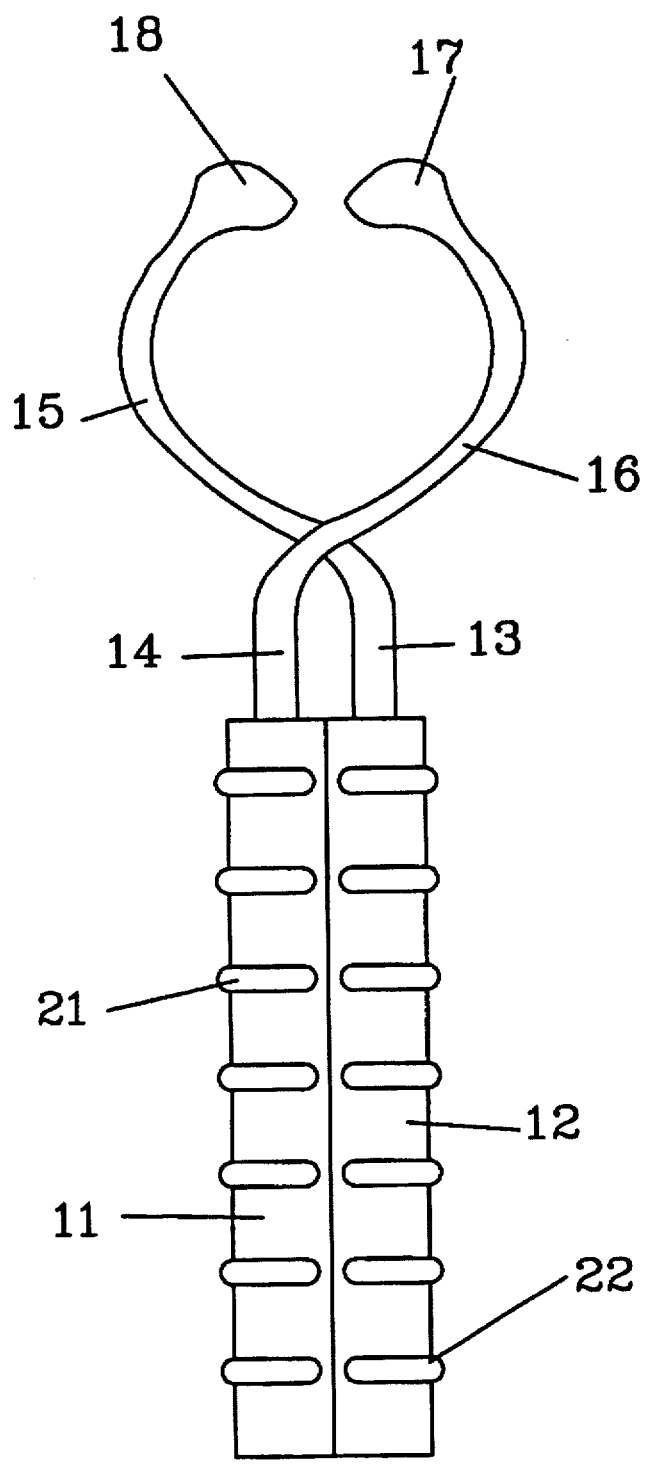
FIG. 3 shows a side view of the two-pieced instrument with handles joined together.

FIG. 3 shows Part A and Part B joined together with tongue 19 in groove 20, and necks 13 and 14 crossed so that the two spoon shaped parts 15 and 16 are adjacent each other with fecal matter between them. The two handles 11 and 12 will not shift, one relative to the other, because the tongue 19 and groove 20 effectively lock the two handles together, preventing them from slipping while held together. An alternate design is to use several pins in one handle and corresponding holes in the other handle which may be used to hold the two handles together to prevent slipping of the handles.

Ridges 21 and 22 provide a non-slip grip for the hand holding and pulling the instrument from the rectal canal. Since the person using the instrument will have a rubber or thin plastic glove on the hand, the ridges prevent the handles from slipping in the hand grasp.

Ridges 21 and 22 may be replaced with a textured or knuckle-shaped surface to prevent the handles from slipping in the hand.

The two spoon shaped parts 15 and 16 do not touch at the thickened and rounded ends 17 and 18, leaving a gap 25 between the two ends of the spoon shaped parts. The gap insures that the two ends 17 and 18 will not meet and pinch the rectal wall.

The use of the two parts of the two-part instrument provides the advantage that separate parts allow for easier sideways insertion through the anus, one side at a time, around and then surrounding the fecal matter. There is less opportunity for damaging the rectal wall because of the round tips, and the fact that the tips do not touch when the handles are secured together by the tongue and groove in the handles. The two unattached parts of the instrument provide for better maneuverability of the instrument during insertion into the rectal canal.

What is claimed:

1. A surgical instrument for removing fecal impaction having an insertion end and a handle end, comprising:

a first handle;

a first curved member attached to the first handle;

a first spoon shaped portion, having a first rounded and thickened end at an insertion end, and a second end attached to the first handle by the first curved member;

a second handle;

a second curved member attached to the second handle;

a second spoon shaped portion, having a first rounded and thickened end at an insertion end, and a second end attached to the second handle by the second curved member;

a tongue and groove arrangement extending the length of the first and second handles, with the tongue extending from one of said first and second handles, and said groove extending into a different one of said first and second handles.

2. The surgical instrument according to claim 1, wherein said first and second handles have ridges thereon for providing a secure gripping surface.

3. The surgical instrument according to claim 1, wherein when the tongue of one handle is placed in the groove of the other handle, the first and second curved members extend adjacent to each other forming a cross, placing the first spoon shaped portion over said second handle, and placing the second spoon shaped portion over said first handle.

4. A two piece surgical instrument having an insertion end for removing fecal impaction and detained stool, comprising:

a first handle having a first spoon shaped portion attached to the first handle by a first curved member, the first spoon shaped portion have a rounded and thickened end at the insertion end;

a second handle having a second spoon shaped portion attached to the second handle by a second curved member, the second spoon shaped portion have a rounded and thickened end at the insertion end;

a tongue and groove arrangement extending the length of the handle with the tongue extending from one of said first and second handles, and said groove extending into a different one of said first and second handles; and a plurality of ridges extending the length of each of said first and second handles.

5. The surgical instrument according to claim 4, wherein each of said first and second spoon shaped portions each have an end that is rounded and thicker than the rest of the spoon shape portion.

6. The surgical instrument according to claim 4, wherein when the tongue of one handle is placed in the groove of the other handle, the first and second curved members extend adjacent to each other forming a cross, placing the first spoon shaped portion over said second handle, and placing the second spoon shaped portion over said first handle.

7. A two piece surgical instrument for removing fecal impaction, comprising:

a first handle having a first spoon shaped portion attached to the first handle by a first curved member, said first spoon shaped portion having a thickened rounded end opposite the end attached to said first handle;

a second handle having a second spoon shaped portion attached to the second handle by a second curved member, said second spoon shaped portion having a thickened rounded end opposite the end attached to said second handle;

a tongue and groove arrangement extending the length of the handles with the tongue extending from one of said first and second handles, and said groove extending into a different one of said first and second handles; and a plurality of ridges extending transverse to the length of each of said first and second handles.

* * * * *